United States Patent
Dove et al.

(10) Patent No.: US 6,190,042 B1
(45) Date of Patent: Feb. 20, 2001

(54) DENTAL X-RAY AIMING DEVICE FOR LONGITUDINAL RADIOGRAPHIC ANALYSIS

(75) Inventors: S. Brent Dove; Marden E. Alder, both of San Antonio, TX (US)

(73) Assignee: Electro Medical Systems, Richardson, TX (US)

(*) Notice: Under 35 U.S.C. 154(b), the term of this patent shall be extended for 0 days.

(21) Appl. No.: 09/406,258

(22) Filed: Sep. 24, 1999

Related U.S. Application Data

(60) Provisional application No. 60/102,206, filed on Sep. 29, 1998.

(51) Int. Cl.[7] .................................................. A61B 6/14
(52) U.S. Cl. ........................ 378/170; 378/167; 378/168; 378/169
(58) Field of Search .................................. 378/167, 168, 378/169, 170, 204, 205

(56) References Cited

U.S. PATENT DOCUMENTS

| | | | |
|---|---|---|---|
| 2,777,068 | 1/1957 | Bowser | 250/64 |
| 3,003,062 | 10/1961 | Updegrave | 250/70 |
| 3,864,576 | 2/1975 | Stevenson | 250/505 |
| 4,012,638 | 3/1977 | Altschuler et al. | 250/491 |
| 4,147,662 | 4/1979 | Schwartz | 250/444 |
| 4,247,780 | 1/1981 | Webber et al. | 250/491 |
| 4,295,050 | 10/1981 | Linden | 250/479 |
| 4,365,162 | 12/1982 | Jarby | 378/170 |
| 4,598,416 | 7/1986 | Donato | 378/168 |
| 4,941,164 | 7/1990 | Schuller et al. | 378/205 |
| 4,949,370 | 8/1990 | Tanaka | 378/170 |
| 4,965,885 | 10/1990 | Fuhrmann | 378/168 |
| 4,995,108 | 2/1991 | Takaka | 378/168 |
| 5,001,738 | 3/1991 | Brooks | 378/170 |
| 5,034,974 | * 7/1991 | Yurosko | 378/166 |
| 5,090,047 | 2/1992 | Angotti et al. | 378/170 |
| 5,119,410 | 6/1992 | Donato | 378/170 |
| 5,127,031 | * 6/1992 | Yurosko | 378/166 |
| 5,289,522 | 2/1994 | Kanbar et al. | 378/170 |
| 5,327,477 | 7/1994 | Levy | 378/168 |
| 5,463,669 | 10/1995 | Kaplan | 378/205 |
| 5,473,662 | 12/1995 | Barish | 378/170 |
| 5,513,240 | 4/1996 | Hausmann et al. | 378/170 |
| 5,598,454 | 1/1997 | Franetzki et al. | 378/206 |
| 5,625,666 | 4/1997 | Willis | 378/167 |
| 5,631,943 | 5/1997 | Miles | 378/102 |
| 5,652,779 | 7/1997 | Levy et al. | 378/170 |
| 5,737,388 | 4/1998 | Kossila | 378/168 |
| 6,033,111 | * 3/2000 | Winters et al. | 378/170 |
| 6,041,102 | * 3/2000 | Francsis | 378/165 |

OTHER PUBLICATIONS

Design Patent Des. 281,353 Nov. 12, 1985 Sico, Jr. D24/2.
Foreign Patent—France 1,088,070 (not translated into English) Nov. 25, 1953.

* cited by examiner

*Primary Examiner*—David P. Porta
*Assistant Examiner*—Allen C. Ho
(74) *Attorney, Agent, or Firm*—Haynes and Boone, LLP

(57) ABSTRACT

An improved dental x-ray aiming device for longitudinal radiographic analysis is provided. The device includes a bite block, a guiding rod, an aiming ring, and a supplemental ring. The bite block includes a film holder that is not perpendicular to a top surface of the bite block. The guiding rod is also attached to the bite block in a non-parallel relationship to accommodate the non-perpendicular arrangement of the film holder. As a result, a proper relationship is maintained between the aiming ring (and hence a dental radiography device) and the film holder. The aiming ring is attached to the guiding rod through a sliding member. The sliding member secures the aiming ring at a predetermined distance from the guiding rod, while allowing the aiming ring to move on an axis parallel with the guiding rod. The bite block includes a slot for receiving and holding a reference device for later density reference measurements.

25 Claims, 4 Drawing Sheets

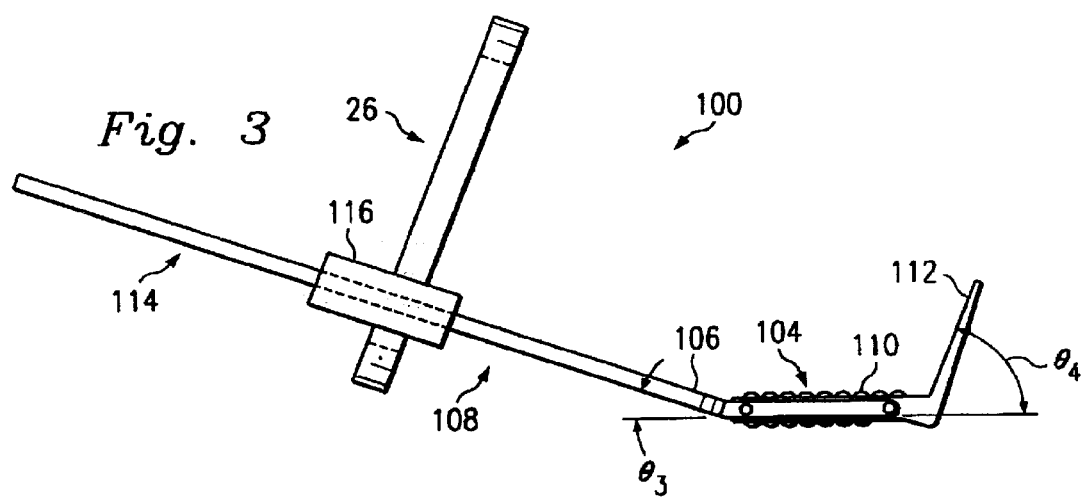
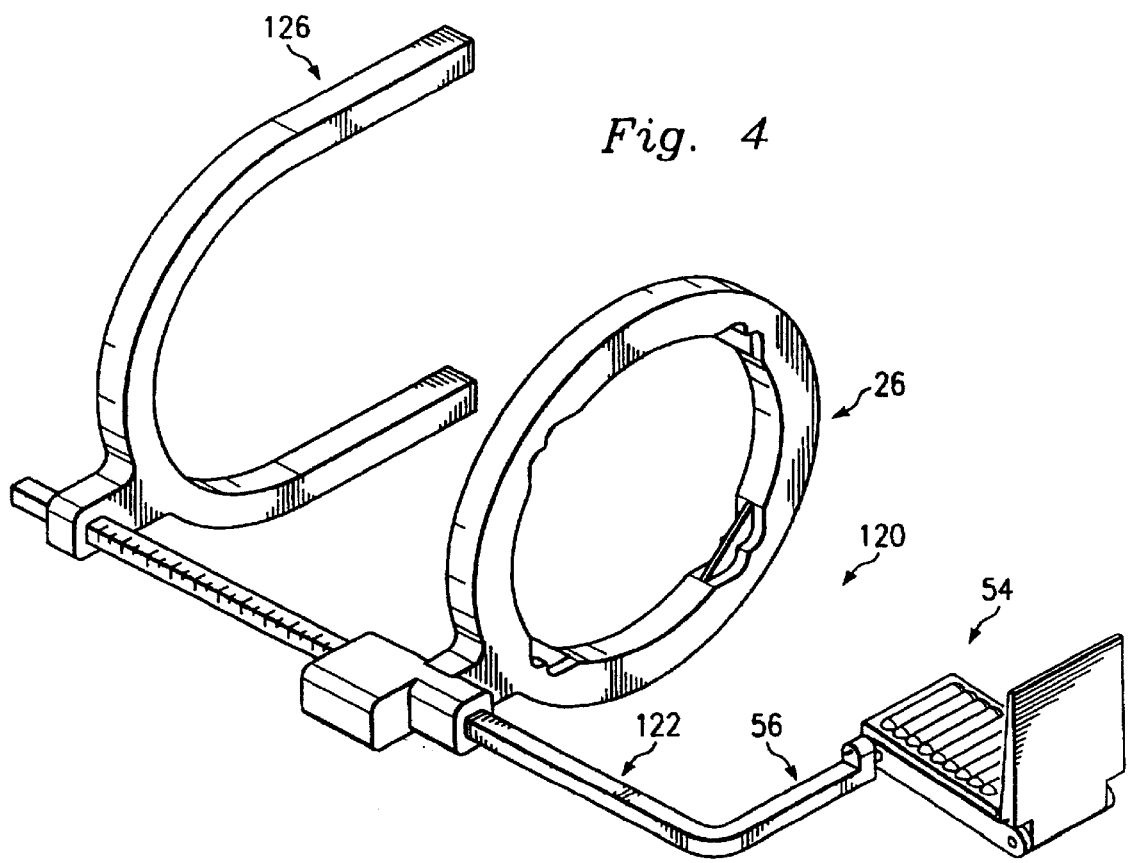

DENTAL X-RAY AIMING DEVICE FOR LONGITUDINAL RADIOGRAPHIC ANALYSIS

CROSS REFERENCE

This application claims the benefit of U.S. Ser. No. 60/102,206 filed Sep. 29, 1998.

BACKGROUND OF THE INVENTION

The invention relates generally to film positioning systems for dental radiography procedures and, more particularly, to an aiming device that assures that a desired alignment is consistently and repeatedly maintained between an x-ray film, a dental arch, and an x-ray equipment.

Dental radiographic images are made using x-ray examination units for obtaining intraoral images of a patient's dental arch (e.g., teeth and gums). Such intraoral images are typically examined shortly after developing the x-ray film for the purpose of diagnosing the patient's oral health.

It is desired, however, to create a series of radiographic images over an extended period of time to better diagnose the patient's oral health. To support proper longitudinal analysis, it is important that the radiographic images are repeatedly aligned and taken with the same relative projection geometry.

Referring to FIG. 1, traditional dental radiography utilizes a rigid aiming device such as the device 10. The device 10 includes a bite block 14 located on a distal end 16 of a guiding rod 18. The bite block 14 includes a biting portion 20 and a film holder 22. A top surface of the biting portion 20 is parallel with the guiding rod 18 and perpendicular to the film holder 22.

Near a proximal end 24 of the guiding rod 18 is an aiming ring 26. The aiming ring 26 is circumferentially engageable about a x-ray position indicating device (or simply "cone") 28 for positioning the film holder 22 in a perpendicular orientation with respect to a line of sight 30 for x-rays emanating from the cone.

In operation, a patient places the bite block 14 inside his mouth 32 and compresses the biting portion 20 between corresponding upper and lower teeth 34. Ideally, a perpendicular orientation between the line of sight 30 and the film holder 22 will be maintained.

However, as is often the case, the film holder 22 provides discomfort because it contacts a surface of the mouth 32 (e.g., the roof of the mouth). When this occurs, the film holder 22 is often adjusted to a new position, such as is shown in phantom with film holder 22a. If the perpendicular orientation is to be maintained, then the biting portion 20 and the guiding rod 18 (and hence the aiming ring 26 and the line of site 30) must move to a new position, such as is shown in phantom with biting portion 20a and guiding rod 18a, respectively. If the biting portion 20a is flexibly connected to the film holder 22a and the guiding rod 18a, the orientation between the film holder 22a and the guiding rod 18a will most likely not be perpendicular. If the biting portion 20a is rigidly connected to the film holder 22a and the guiding rod 18a, the orientation may be perpendicular, but the exact position of the film holder 22a inside the mouth 32 will vary from one radiographic image to the next.

Therefore, what is needed is an aiming device that secures and maintains a desired orientation between the film holder and the guiding rod, yet accommodates different sized and shaped mouths and/or different projection geometries.

SUMMARY OF THE INVENTION

A technical advance is achieved by an improved dental x-ray aiming device for longitudinal radiographic analysis. The device includes a bite block, a guiding rod, and an aiming ring. In one embodiment, the bite block includes a film holder that is not perpendicular to a top surface of the bite block. The guiding rod is also attached to the bite block in a non-parallel relationship to accommodate the non-perpendicular arrangement of the film holder. The aiming ring is attached to the guiding rod. As a result, a proper relationship is maintained between the aiming ring (and hence a dental radiography device) and the film holder.

In some embodiments, the aiming device includes a supplemental aiming ring attached to the guiding rod. The supplemental ring has an open portion for receiving the dental radiography device and a closed portion for restricting the dental radiography device to a fixed location.

In some embodiments, the bite block includes a top portion, a bottom portion, and two side walls for defining a slot. The slot can receive and hold a reference device for density reference measurements. The slot may be aligned so that a line of sight of a beam emanating from the dental radiography device is parallel with the slot.

In some embodiments, an indicator is provided to record the angular relationship of the bite block and the film holder on a radiographic image produced using the aiming device.

In some embodiments, the bite block is pivotally attached to the film holder and the guiding rod. The pivotal attachments allow an angular relationship between the top surface of the bite block and the film holder to be adjusted while maintaining an angular relationship between the film holder and the guiding rod. In some embodiments, one or more adjustable locking mechanisms can be used for selectively locking the angular relationship of the film holder and/or the guiding rod. In some embodiments, a connecting rod maintains the overall angular relationship of the guiding rod, the top surface of the bite block, and the film holder.

In some embodiments, the aiming ring is attached to the guiding rod through a sliding member. The sliding member secures the aiming ring at a predetermined distance from the guiding rod, while allowing the aiming ring to move on an axis parallel with the guiding rod. In some embodiments, the guiding rod includes an upward extending portion that aligns a central portion of the aiming ring with a central portion of the film holder.

The present invention also includes a method for using an improved aiming device to conduct dental radiography procedures on a dental arch, taken over time. Several aiming devices, such as those discussed above, are defined at certain, predefined angular relationships. A specific aiming device is selected and a dental image of a patient's dental arch is taken using the dental radiography device and the selected aiming device. The dental image is sent to a diagnostic radiographic entity, such as for digital subtraction radiography, and the selected aiming device is recorded. As a result, the same aiming device (or another device with the same angular relationship), can be used for subsequent radiographic images, thereby facilitating digital subtraction radiography analysis.

BRIEF DESCRIPTION OF THE DRAWINGS

FIG. 3 is a side view of an aiming device for dental radiography according to another embodiment of the present invention.

FIG. 4 is an isometric view of an aiming device for dental radiography according to yet another embodiment of the present invention.

DESCRIPTION OF THE EMBODIMENTS

Figure 2:
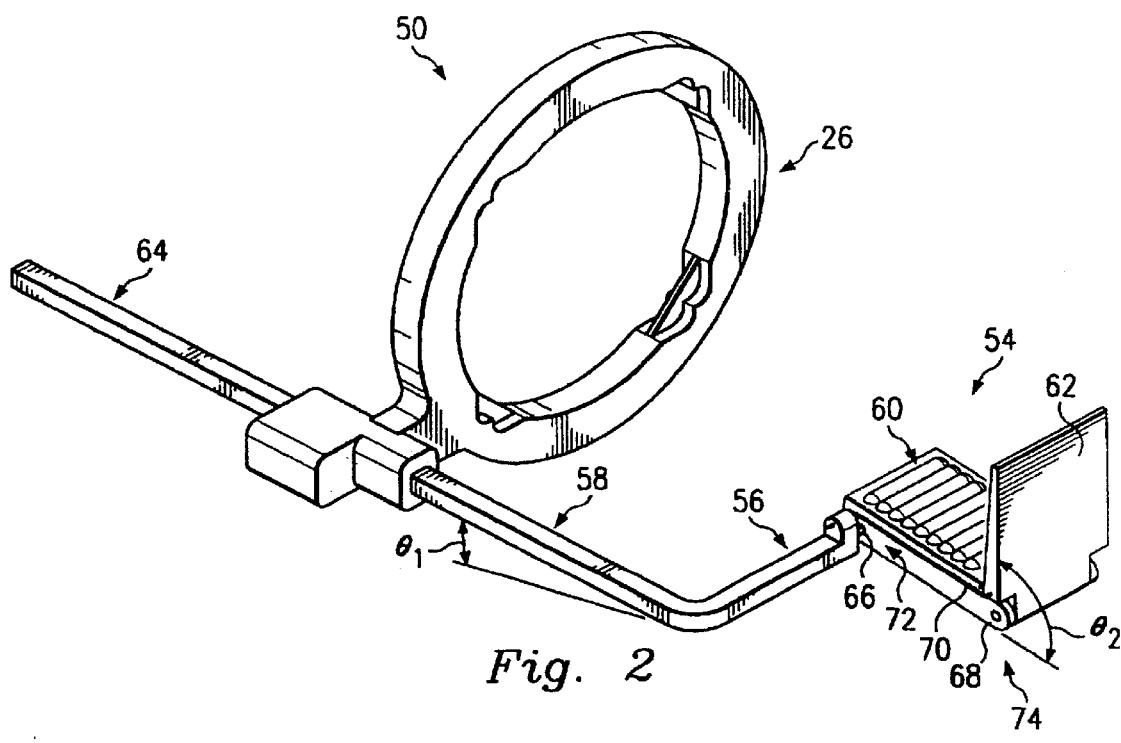
FIG. 2 is an isometric view of an aiming device for dental radiography according to one embodiment of the present invention.

Referring to FIG. 2, the reference numeral 50 designates, in general, an aiming device for making dental radiographic images, such as can be used to create a series of radiographic images over an extended period of time to better diagnose a patient's oral health. It is understood that the following description provides many different embodiments, or examples, for implementing different features of the invention. Techniques and requirements that are only specific to certain embodiments should not be imported into other embodiments. Also, specific examples of components and positions are described to help clarify the invention. These are, of course, merely examples and are not intended to limit the invention from that described in the claims.

The device 50 includes a bite block 54 located on a distal end 56 of a guiding rod 58. The bite block 54 includes a biting portion 60 and a film holder 62. Near a proximal end 64 of the guiding rod 58 is an aiming ring 26.

The device 50 has the ability to adjust to different positions to accommodate mouths of different sizes and shapes. To provide this adjustability, the distal end 56 of the guiding rod 58 is pivotally connected to the biting portion 60 with a pivot pin 66. Also, the film holder 62 is attached to the biting portion 60 with a pivot pin 68. Attached between the film holder 62 and the distal end 56 is a connecting rod 70. The connecting rod 70 provides a direct linkage between the film holder 62 and the distal end 56, regardless of their positions.

In operation, if a perpendicular relationship is desired between the film holder 62 and the guiding rod 58, the connecting rod 70 will maintain the relationship. For the sake of reference, an angle $\theta_1$ can be defined between the guiding rod 58 and a plane parallel with the top and bottom surfaces of the biting portion 60, and an angle $\theta_2$ can be defined between the film holder 62 and the same plane. Whenever the film holder 62 is moved pivotally with respect to the bite block 54, the perpendicular relationship will be maintained so that:

$$\theta_1 + \theta_2 = 90°. \tag{1}$$

By so doing, various angle sets of $(\theta_1, \theta_2)$ can be used. For instance, (0°, 90°), (10°, 80°), or (20°, 70°) can be easily obtained. When a particular angle set is determined by the guiding rod 58, the angles $\theta_1$, $\theta_2$ are rigidly maintained. Furthermore, the selected angle set can be recorded so that subsequent radiographic images taken from the same patient can use the same angle set, thereby providing consistently aligned and positioned radiographic images.

In some embodiments, one or more locking mechanisms 72, 74 are employed with the pivot pins 66, 68, respectively, to provide for predetermined angles $\theta_1$ and $\theta_2$. The locking mechanisms 72, 74 may be, for example, notches or protrusions in either or both the bite block 54 and/or the pivot pins 66, 68. In embodiments with two locking mechanisms, no connecting rod is required. The film holder 62 can be individually rotated and locked into position to obtain a particular $\theta_2$, and then the guiding rod 58 can be rotated so that a complementary $\theta_1$ is locked into position. In other embodiments with only one locking mechanism, by individually rotating and locking one of the pivot pins 66, 68 with the one mechanism, the connecting rod 70 can secure the other of the pivot pins, thereby maintaining the desired relationship.

Referring to FIG. 3, the reference numeral 100 designates, in general, another embodiment of an aiming device for making dental radiographic images. As with the device 50 of FIG. 2, the device 100 can be used to create a series of radiographic images over an extended period of time to better diagnose a patient's oral health.

The device 100 includes a bite block 104 located on a distal end 106 of a guiding rod 108. The bite block 104 includes a biting portion 110 and a film holder 112. Near a proximal end 114 of the guiding rod 108 is an aiming ring 26. The aiming ring 26 is maintained in a perpendicular relationship with the guiding rod 108 through a sliding member 116. In certain applications, this perpendicular relationship is critical for obtaining the series of radiographic images in the proper orientation.

The device 100 is similar to the device 10 (FIG. 1), with the exception that the guiding rod 108, is not parallel with the top or bottom surface of the biting portion 110, and the film holder 112 is not perpendicular with the top or bottom surface of the biting portion 110. For the sake of reference, an angle $\theta_3$ can be defined between the guiding rod 108 and a plane parallel with the top or bottom surface of the biting portion 110, and an angle $\theta_4$ can be defined between the film holder 112 and the same plane. However, the angle $\theta_3$ and the angle $\theta_4$ are rigidly fixed and:

$$\theta_3 + \theta_4 = 90°. \tag{2}$$

A plurality of devices 100 can accommodate different angle sets, such as angle sets $(\theta_3, \theta_4)$ of (0°, 90°), (10°, 80°), and (20°, 70°). In this way, a specific device 100 with a specific angle set can be chosen so that a series of radiographic images taken from the same patient can use the same angle set, thereby providing consistently aligned and positioned radiographic images. It is also noted that, in the present embodiment, the film holder 112 and the biting portion 110 can be formed as a single monolithic substrate.

Referring to FIG. 4, the reference numeral 120 designates, in general, yet another embodiment of an aiming device for making dental radiographic images. As with the device 50 of FIG. 2 and the device 100 of FIG. 3, the device 120 can be used to create a series of radiographic images over an extended period of time to better diagnose a patient's oral health.

Figure 1:
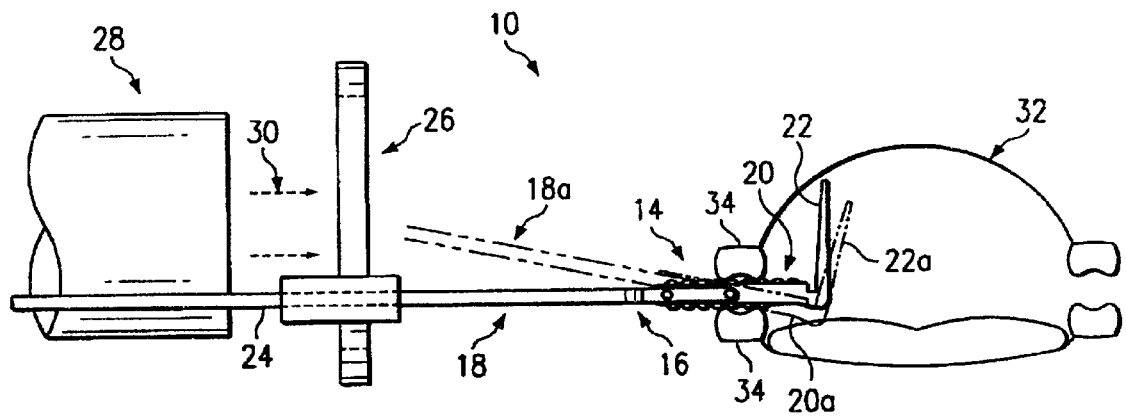
FIG. 1 is a side view of a conventional aiming device used for dental radiography.

The device 120 includes many of the same components of the two previous embodiments 50, 100. For the sake of example, the device 120 will be described with certain components of the device 50 (FIG. 2). The device 120 includes a second, supplemental aiming ring 126 to further secure the device to an x-ray system through the x-ray cone 28 (FIG. 1). Such a supplemental aiming ring 126 is designed for additional restriction to the alignment of the radiography device. Unlike the aiming ring 26, the supplemental ring 126 is shaped as an open-sided circle, thereby facilitating its engagement with the x-ray cone 28 and improving the alignment of the overall x-ray system with the guiding rod 122.

Figure 5:
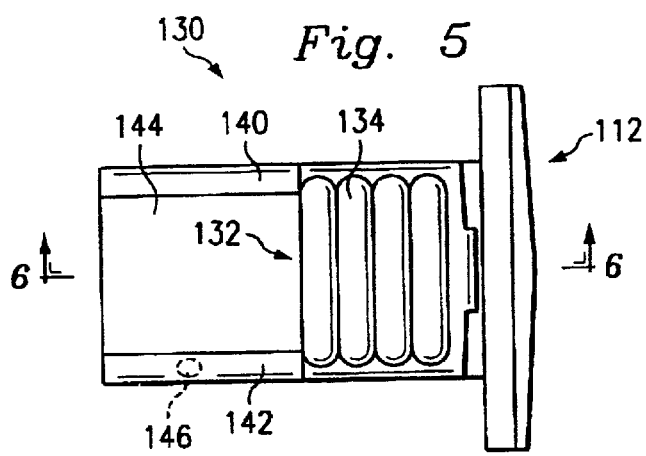
FIG. 5 is a top perspective view of a bite block having a receiving slot for a layer density reference device according to another embodiment of the present invention.
Figure 6:
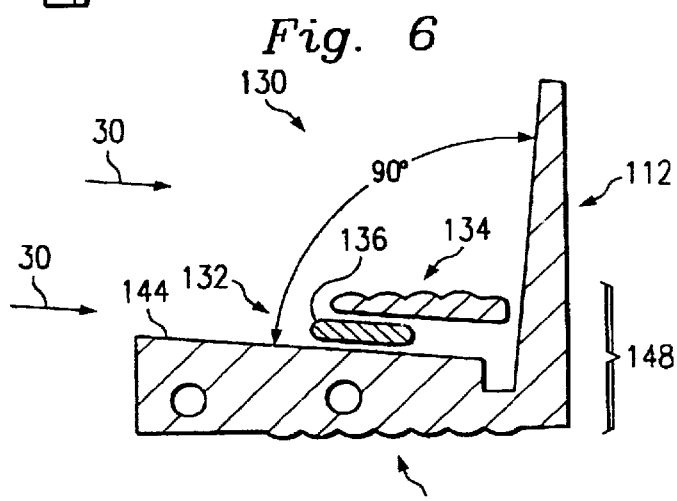
FIG. 6 is a side, cross-sectional view of the bite block of FIG. 5.

Referring now to FIGS. 5 and 6, the reference numeral 130 designates, in general, yet another embodiment of a bite block for use with the device 100 of FIG. 3. For the sake of example, the bite block 130 will be described in association with the device 100 having an angle set:

$$(\theta_3, \theta_4) = (15°, 75°). \tag{3}$$

The bite block 130 includes a receiving slot 132 between a top biting portion 134 and a bottom biting portion 135. In the present example, the top surface of the biting portion 134 is smaller than the top surface of the biting portion 110 (FIG. 3). However, there is still sufficient surface to receive a patient's teeth, as described in FIG. 1.

The receiving slot 132 is for receiving and storing a radiographic attenuation reference (or simply "reference device") 136, which provides for quantitative densitometric analysis. For example, the reference device 136 may be a wedge that easily slides into the receiving slot 132. When an x-ray exposure is made, the image of the reference device 136 will also be recorded in the radiographic image. Since the reference device 136 is inside the bite block 130, it can be readily identified in the radiographic image, without the radiographic obstruction of the patient's teeth. It is understood that the reference device 136 can be used with both fixed and variably-adjustable aiming devices.

Referring specifically to FIG. 5, the bite block 130 includes a pair of side walls 140, 144 surrounding the receiving slot 132. The side walls 140, 142 provide support for the top portion 134 and can be used to direct the density reference device 136 into the slot 132.

In some embodiments, a unique identifier 146 may be physically incorporated into the bite block 130. The identifier 146 may be in the form of one or more lead bits formed inside one of the side walls 140, 142 or other portion of the bite block. The identifier 146 can be used to indicate a particular angle set ((15°, 75°) for the present example). The identifier 146 may be in the form of a numeral designator, or can simply be a predetermined number of bits that corresponds to a specific angle set. By being made of lead (or other suitable radio-opaque material), the indicator will appear on later-produced radiographic images, thereby identifying the angle set used for those images. The identifier 146 may also provide visual identification to the dentist, indicating the particular angle set. For example, each lead bit may form a protrusion that is visually recognizable from outside the bite block 130.

Referring specifically to FIG. 6, the receiving slot 132 is configured in a desired orientation (e.g., perpendicular) with the film holder 112 and the aiming ring 26 (FIG. 2). As a result, x-rays traveling down the line of sight 30 are unobstructed by the bite block 130 all the way through the receiving slot 132, (except, of course, by the reference device 136) to the film holder 112. Any dental radiographic images produced using the device 50 with the bite block 130 will therefore have a very clear density reference for performing densitometric analysis.

It is noted that in some embodiments, a thickness 148 of the bite block 130 is relatively large, as compared with the thickness of conventional devices. This relatively large thickness 148 helps to disarticulate the patients teeth, thereby improving the diagnostic quality of the radiographic image produced therefrom. Such disarticulation is especially beneficial for certain angle sets.

Figure 7:
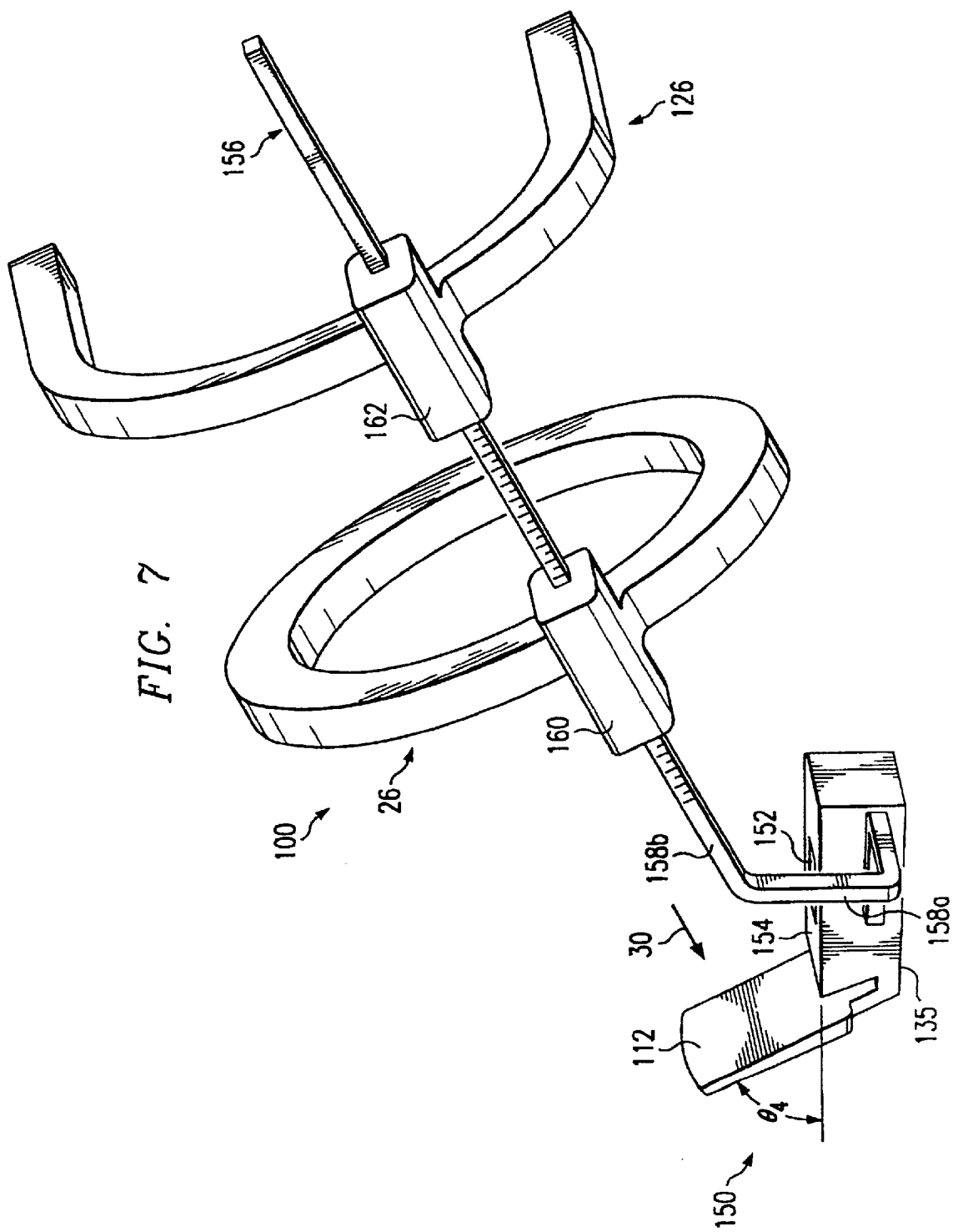
FIG. 7 is an isometric view of the aiming device of FIG. 3 including a bite block with a receiving slot for a layer density reference device according to another embodiment of the present invention.

Referring now to FIG. 7, the aiming device 100 of FIG. 3 is shown having a different bite block 150. The bite block 150 is formed from a single, monolithic substrate and has an angle set:

$$(\theta_3, \theta_4) = (25°, 65°). \tag{4}$$

The bite block 150 includes a receiving slot 152 between a top biting portion 154 and the bottom portion 135. In the present example, the top surface of the biting portion 154 is smaller than the top surface of the biting portion 134 (FIG. 5). However, there is still sufficient surface to receive a patient's teeth, as described in FIG. 1.

The bite block 150 is connected to a guiding rod 156. The guiding rod 156 includes an upward extending portion 158a and a sliding portion 158b. The aiming ring 26 is maintained in close proximity to the sliding portion 158b of the guiding rod through a sliding member 160, despite the angle set. The upward extending portion 158a effectively raises the sliding portion 158b, and hence the aiming ring 26, so that a central portion of the aiming ring aligns with a central portion of the film holder 112, in accordance with the line of sight 30.

The sliding member 160 also allows the aiming ring 26 to easily move up and down the sliding portion 158b. It is further noted that the supplemental aiming ring 126 also includes a sliding member 162 for functionality similar to the sliding member 160.

As discussed above with respect to FIG. 2, multiple aiming devices having different angle sets (or one or more variable-angled devices) can be provided so that a series of radiographic images taken from the same patient can repeatedly use a particular angle set. This feature is also accommodated by different receiving slots configured at different angles in the bite block.

Figure 8:
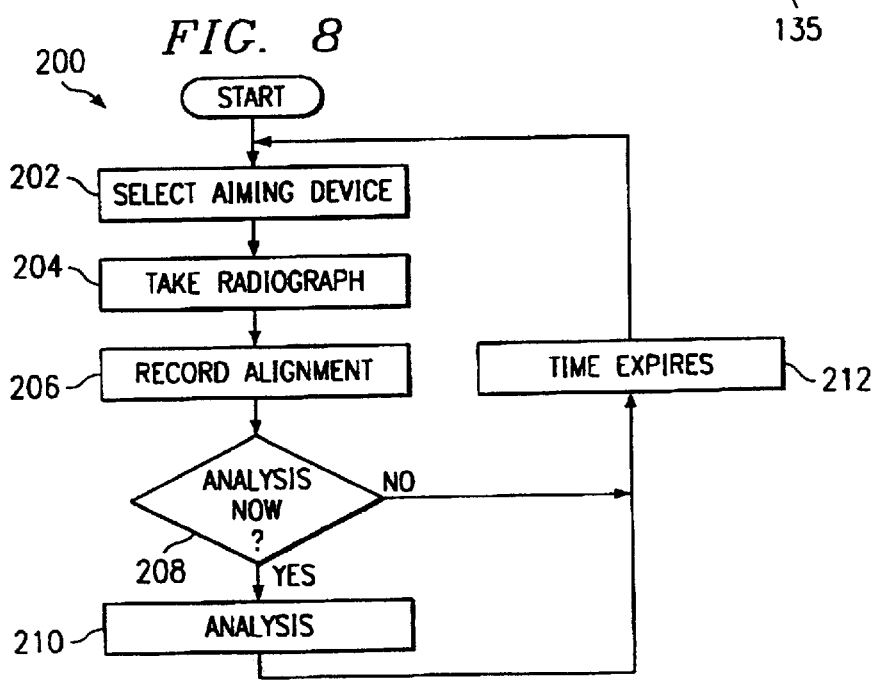
FIG. 8 is a flow chart of a method for conducting digital subtraction radiography using one or more of the embodiments of FIGS. 2–7.

Referring now to FIG. 8, a method 200 can be used for performing radiographic analysis, such as digital subtraction radiography, on a patient's dental arch. Execution begins at step 202, where a dentist or technician selects a specific aiming device. Any of the above described aiming devices can be used, but for the sake of example, the aiming device 100 (FIG. 3) having the bite block 130 (FIG. 5) will be discussed.

At step 204, the radiographic image is taken by the dental radiography device 28 (FIG. 1). In the present example, the film holder 112 is angled such that $\theta_4 = 15°$. As a result, the film holder is more comfortable in the patient's mouth and a certain perspective is obtained by the radiographic image. Also, the density reference device 136 forms a reference for the radiographic image, discussed in greater detail, below. Because the reference device 136 is located inside the bite block, it does not interfere with the image of the teeth, and vice versa.

At step 206, the alignment of the aiming device is recorded. For the present example, the angle set (75°, 15°) is recorded. If the bite block 130 with the indicator 146 is used, then the indicator will appear on the radiographic image and thus provide the desired recordation.

At step 208, a determination is made as to whether or not to perform immediate radiographic analysis. Such determination can be dependent on various factors. For example, a negative determination may still include an initial cursory analysis, but for the sake of the present example, no extensive or comparative analysis will be made.

Upon a positive determination at step 208, execution proceeds to step 210 and analysis is performed by a diagnostic radiographic entity. It is understood that there are various analysis techniques, and the diagnostic radiographic entity may simply be, for example, a person visually analyzing one or more images and/or a computer aided facility that has the ability to compare multiple images and perform analysis on those images. For the present example, the diagnostic radiographic entity is the latter facility which is performing digital subtraction radiographic analysis.

The radiographic image(s) produced at step 204 are compared with previous radiographic images to analyze the patient's dental arch (e.g., teeth and gums) over a period of time. The previous images may have been created by previous iterations of the method 200, by previous x-rays using conventional aiming ring devices, or a combination of the two. However, by using the aiming device of the present invention, each of the radiographic images are very consistent in their alignment and projection geometries. Also, since the reference device 136 appears in each radiographic image, this further facilitates the comparative process between respective radiographic images.

Upon completion of step 210, or upon a negative determination at step 208, execution proceeds to step 212. At step 212, a period of time expires between radiographic images (or sets of images) and then execution returns to step 202. For example, a patient may visit a dentist on an annual basis, and a set of radiographic images (as in step 204) is created at each visit. Since the alignment of the aiming device was recorded at step 206, the same aiming device, or a similarly-adjusted aiming device, can be used for all of the radiographic images.

An advantage of the present invention is that it allows a dentist to quickly aim an x-ray device at a patient's dental arch in a consistent, highly precise manner.

Another advantage of the present invention is that a dentist is able to adjust the aiming device and/or film holder to accommodate different size mouths.

Yet another advantage of the present invention is that a dentist is able to select an aiming device and/or film holder to accommodate different projection orientations.

Still another advantage of the present invention is that different positions and orientations can be easily recorded. This is especially advantageous for digital subtraction radiography utilizing multiple radiographic images taken over a long period of time.

It is understood that several variations may be made in the foregoing. Modifications, changes and substitutions are intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. An aiming device for performing dental radiography procedures, comprising:
    a bite block having a film holder angularly attached to a first end of the bite block;
    a guiding rod having a distal end angularly attached to a second end of the bite block;
    an aiming ring for receiving a dental radiography device; and
    a sliding member for securing the aiming ring in a perpendicular relationship with the guiding rod while allowing the aiming ring to move on an axis parallel with the guiding rod;
    wherein the film holder is fixed at the first end of the bite block with a first predetermined angle $\alpha$ with respect to a biting surface of the bite block, such that $\alpha \neq 90°$, and wherein the distal end of the guiding rod is fixed at the second end of the bite block with a second predetermined angle $\beta$ with respect to the biting surface of the bite block, such that $\alpha+\beta=90°$.

2. The aiming device of claim 1 wherein the aiming ring maintains the dental radiography device at a predetermined distance from the guiding rod despite the values for angles $\alpha$ and $\beta$.

3. The aiming device of claim 1 wherein the guiding rod includes an extending portion for aligning a central portion of the aiming ring with a central portion of the film holder.

4. The aiming device of claim 1 wherein the film holder is permanently fixed to the first end of the bite block.

5. An aiming device for dental radiography procedures, comprising:
    a bite block having a film holder angularly attached to a first end of the bite block;
    a guiding rod having a distal end angularly attached to a second end of the bite block;
    an aiming ring attached to the guiding rod, for receiving a dental radiography device and securing the dental radiography device in a perpendicular relationship with the guiding rod; and
    a supplemental aiming ring attached to the guiding rod, the supplemental ring having an open portion for receiving the dental radiography device and a closed portion for restricting the reception of the dental radiography device;
    wherein the film holder and the dental radiography device received by the aiming ring are aligned such that a line of sight for a beam emanating from the device is perpendicular to the film holder.

6. The aiming device of claim 5 wherein the film holder is fixed at the first end of the bite block with a first predetermined angle $\alpha$ with respect to a biting surface of the bite block, such that $\alpha \neq 90°$, and wherein the distal end of the guiding rod is fixed at the second end of the bite block with a second predetermined angle $\beta$ with respect to the biting surface of the bite block, such that $\alpha+\beta=90°$.

7. The aiming device of claim 5 wherein the guiding rod maintains a perpendicular orientation with respect to the film holder, the film holder is oriented at an acute angle with respect to a biting surface of the bite block, and the guiding rod is oriented at an angle with respect to the biting surface of the bite block.

8. The aiming device of claim 5 wherein the guiding rod has an extending portion and a sliding portion, wherein the sliding portion receives the aiming ring and the supplemental ring, and the extending portion raises the sliding portion to a position so that a predetermined portion of the dental radiography device aligns with a predetermined portion of the film holder.

9. The aiming device of claim 5 wherein the bite block includes a top portion, a bottom portion, and two side walls for defining a slot, the slot for receiving a density reference device.

10. The aiming device of claim 9 wherein the slot is aligned so that the line of sight for the beam emanating from the device is parallel with the slot.

11. The aiming device of claim 5 wherein at least one of the angular attachments to the bite block is pivotally adjustable.

12. An apparatus for dental radiography procedures, comprising:
    a bite block;
    a film holder pivotally attached to a first end of the bite block;
    a guiding rod having a distal end pivotally attached to a second end of the bite block;

means attached to the guiding rod for receiving a dental radiography device; and a connecting rod connecting and co-relating the distal end of the guiding rod at the first end and the film holder at the second end of the bite block, wherein an angular relationship between the bite block and the film holder can be adjusted while maintaining an angular relationship between the film holder and the guiding rod.

13. The apparatus of claim 12 wherein a line of sight for beams emanating from the dental radiography device maintains a perpendicular orientation with respect to the film holder.

14. The apparatus of claim 12 further comprising:

an adjustable locking mechanism for selectively locking a pivotal orientation of the film holder at a desired position.

15. The apparatus of claim 12 further comprising:

an adjustable locking mechanism for selectively locking a pivotal orientation of the guiding rod at a desired position.

16. The apparatus of claim 12 further comprising:

a supplemental aiming ring attached to the guiding rod to further secure the apparatus to the dental radiography device.

17. The apparatus of claim 12 wherein the bite block has a slot for receiving and maintaining a radiographic attenuation reference device.

18. An aiming device for dental radiography procedures, the aiming device comprising:

a bite block;

a film holder pivotally attached to a first end of the bite block;

a guiding rod having a distal end pivotally attached to a second end of the bite block;

an aiming ring attached to the guiding rod for receiving a dental radiography device;

a first locking mechanism for selectively maintaining an angular orientation of the film holder with the first end of the bite block; and a second locking mechanism for selectively maintaining an angular orientation of the guiding rod with the second end of the bite block, wherein the angular orientation between the bite block and the film holder can be adjusted while maintaining the angular orientation between the film holder and the guiding rod.

19. A method for using an aiming device to conduct dental radiography procedures on a dental arch, the method comprising the steps of:

selecting an aiming device from a set of aiming devices, each aiming device of the set having a bite block, a film holder angularly attached to a first end of the bite block, a guiding rod having a distal end angularly attached to a second end of the bite block, and an aiming ring attached to the guiding rod for receiving a dental radiography device, and wherein at least two of the aiming devices of the set have a different angular relationship between the bite block and the film holder;

taking a dental image of the dental arch using the dental radiography device and the selected aiming device;

providing the dental image to a diagnostic radiographic entity; and recording which of the aiming devices was selected so that additional dental images can be taken, with each image being taken with the same angular relationship between the bite block and the film holder.

20. The method of claim 19 wherein the dental radiography device includes an x-ray system.

21. The method of claim 20 wherein the bite block has an indicator for identifying which of the aiming devices was selected, and wherein the step of recording is performed by the indicator when taking the dental image.

22. An apparatus for dental radiography procedures, comprising:

a bite block having a receptacle for receiving a density reference device, the reference device being positioned underneath a top surface of the bite block;

a film holder angularly attached to a first end of the bite block;

a guiding rod having a distal end attached to a second end of the bite block; and an aiming ring for receiving a dental radiography device and securing the dental radiography device with the guiding rod;

wherein the film holder and the dental radiography device received by the aiming ring are aligned such that a line of sight for a beam emanating from the device is perpendicular to the film holder and the receptacle is parallel with the line of sight, and wherein the density referenced device serves as an indicator for identifying an angular relationship between a biting surface of the bite block and the film holder.

23. An apparatus for dental radiography procedures, comprising:

a bite block having a receptacle for receiving a density reference device, the reference device being positioned underneath a top surface of the bite block;

a film holder angularly attached to a first end of the bite block;

a guiding rod having a distal end attached to a second end of the bite block; and an aiming ring for receiving a dental radiography device and securing the dental radiography device with the guiding rod;

wherein the film holder and the dental radiography device received by the aiming ring are aligned such that a line of sight for a beam emanating from the device is perpendicular to the film holder and parallel with the receptacle, wherein the film holder is not at a perpendicular relationship with a biting surface of the bite block, and wherein the receptacle maintains a perpendicular orientation with the film holder.

24. The apparatus of claim 23 wherein the angular attachment between the film holder and the bite block is pivotally adjustable.

25. An apparatus for dental radiography procedures, comprising:

a bite block;

a film holder angularly attached to a first end of the bite block;

a guiding rod having a distal end attached to a second end of the bite block; and a device for positioning a dental radiography device with the guiding rod; and an indicator for identifying an angular relationship between a biting surface of the bite block and the film holder, the indicator being opaque to the beam emanating from the dental radiography device so that an image of the indicator appears on a radiographic image produced by the device.

\* \* \* \* \*

UNITED STATES PATENT AND TRADEMARK OFFICE
CERTIFICATE OF CORRECTION

PATENT NO. : 6,190,042 B1
DATED : February 20, 2001
INVENTOR(S) : S. Brent Dove, Marden E. Alder It is certified that error appears in the above-identified patent and that said Letters Patent is hereby corrected as shown below:

<u>Title page,</u>
Please correct assignee information as follows:

[73] Assignee: Board of Regents
The University of Texas System
Austin, Texas

Signed and Sealed this

Sixth Day of November, 2001

Attest:

NICHOLAS P. GODICI
*Attesting Officer*    *Acting Director of the United States Patent and Trademark Office*